United States Patent [19]

Teirstein

[11] Patent Number: 5,499,995

[45] Date of Patent: Mar. 19, 1996

[54] BODY PASSAGEWAY CLOSURE APPARATUS AND METHOD OF USE

[76] Inventor: Paul S. Teirstein, 402 Coast Blvd., South, La Jolla, Calif. 92037

[21] Appl. No.: 249,521

[22] Filed: May 25, 1994

[51] Int. Cl.⁶ ............................................. A61M 29/00
[52] U.S. Cl. ............................................. 606/192; 606/194
[58] Field of Search .................................. 606/192, 193, 606/194; 604/96–100, 103–104

[56] References Cited

U.S. PATENT DOCUMENTS

| | | |
|---|---|---|
| 4,638,803 | 1/1987 | Rand . |
| 4,686,985 | 8/1987 | Lottick ............................. 606/192 |
| 4,733,665 | 3/1988 | Palmaz . |
| 4,739,762 | 4/1988 | Palmaz . |
| 4,836,204 | 6/1989 | Landymore et al. . |
| 5,037,427 | 8/1991 | Harada et al. . |
| 5,059,211 | 10/1991 | Stack et al. . |
| 5,102,417 | 4/1992 | Palmaz . |
| 5,116,318 | 5/1992 | Hillstead ........................... 606/192 |
| 5,176,637 | 1/1993 | Sagae ............................... 606/192 |
| 5,176,692 | 1/1993 | Wilk et al. . |
| 5,234,456 | 8/1993 | Silvestrini . |
| 5,234,457 | 8/1993 | Andersen . |
| 5,259,839 | 11/1993 | Burns ............................... 606/192 |
| 5,336,163 | 8/1994 | DeMane ............................. 606/192 |
| 5,360,403 | 11/1994 | Mische .............................. 606/192 |
| 5,366,472 | 11/1994 | Hillstead ........................... 606/192 |
| 5,391,178 | 2/1995 | Yapor ............................... 606/192 |

*Primary Examiner*—Michael A. Brown
*Attorney, Agent, or Firm*—Gerald W. Spinks

[57] ABSTRACT

A method and apparatus for blocking a body passageway by inserting an expandable frame into the passageway and expanding the frame with an expandable balloon to partially embed the frame in the walls of the passageway. The frame can carry a separate sealing membrane, or the balloon can function as the sealing membrane. The sealing membrane, the frame or the balloon can also carry a clot promoting substance. The balloon can be removed along with the inflation tube after the expansion procedure, if it is not serving as the sealing membrane, or the balloon can be detached from the inflation tube and left in place, either as a sealing membrane or simply to lock the frame in place. The frame can be maintained in its expanded state by being plastically deformed during the expansion step, or the frame can be maintained in its expanded state by having the balloon locked in the expanded state and left in place.

40 Claims, 7 Drawing Sheets

BODY PASSAGEWAY CLOSURE APPARATUS AND METHOD OF USE

FIELD OF INVENTION

This invention is in the field of devices used to close or occlude various passageways within the body. Specifically, this invention is particularly suited for occluding blood vessels.

BACKGROUND OF THE INVENTION

There are several types of unwanted or unnecessary passageways within the body. Very often these passageways are not only unnecessary, they are also harmful. Unnecessary passageways in blood vessels or in the heart can be especially harmful, since they can cause the reduction of blood flow, or the bypass of blood flow around an organ. When unwanted passageways exist, they often are congenital in origin, and their correction must often be undertaken in infants. This makes conventional surgical procedures more troublesome, because of the small size of the vessels, because of the additional risk involved in anesthesia, and because other birth defects are often also present.

By way of example, a common type of congenital defect is patent ductus arteriosus, in which an unwanted passageway or duct connects the aorta to the main pulmonary artery, close to the heart. This defect results in the recirculation of oxygenated blood through the lungs, depriving the other organs and tissues of part of their required blood flow. Increased work for the heart results, and enlargement of the heart often ensues.

Surgical correction of patent ductus arteriosus requires entry into the thoracic cavity, usually through the side, involving considerable trauma to the surrounding musculature and connective tissue. Surgery also involves considerable risk, because of the necessity of clamping the duct next to each of the major arteries, and because of the risk of failing to suture the duct successfully. In infants, the duct material is often fragile, and permanent suturing is especially difficult. Even small injuries to surrounding tissues can be extremely serious, and unexpected complications can happen quickly and accelerate rapidly. In this particular defect, surgical correction also always involves the manipulation of a nearby nerve, with the attendant risk of nerve damage.

Other devices have been devised to occlude the unwanted passageway without thoracic surgery, with some success, but all such devices have suffered from the tendency to become dislodged from the passageway. If a device becomes dislodged, in attempting to correct this particular defect, the device will enter the pulmonary artery and lodge somewhere downstream, requiring surgical removal. Typically, such closure devices are advanced, on the end of a wire, either through a femoral or umbilical artery to the aorta, or through a femoral or umbilical vein and through the heart to the pulmonary artery. Guide catheters and guidewires for installing such devices are well known in the art, as are the methods for their use. Once advanced through either the artery or the vein to the ductus arteriosus, the closure device is positioned in the duct and attached in place by some mechanism.

One such known device is a conical foam plug stabilized by an inner steel frame. Another device is a double umbrella type spring loaded wire frame covered by two foam discs. Still another device is a grappling hook device. All of these devices are deployed within a tube of some kind and allowed to expand in place in the passageway by being pushed or pulled out of the tube. Expansion is accomplished either by means of spring action or by manipulation of the wire. Many known devices are held in place by clotting in the closure material, combined with some kind of spring action pressing against the walls of the passageway.

While achieving some success, each of the known devices still becomes dislodged in a fairly high number of cases. There are several underlying reasons why the known devices are not able to permanently block the passageway, in many cases. First, in a defect of this particular type, as well as some others, the flow of blood through the unblocked passageway can be at a relatively high velocity, resulting in some damage to the endothelial tissue surrounding at least one end of the passageway. Second, the passageway can also often be attached to the arteries at a slight angle. These problems, as well as others, can result in a less than optimum sealing surface for the closure device. Unfortunately, most of the known devices attempt to seal along a relatively small surface area, often almost along a line of contact. For example, the double umbrella device, as well as other disc type sealing devices, requires a fairly smooth sealing surface to be successful, and optimally the duct should be attached at right angles to the arteries. Lacking a smooth sealing area around the mouths of the passageway, especially where an oblique angle exists, use of this type of device often results in unwanted residual flow through the shunt, often in the form of high speed jets.

Another problem which besets the known devices is the inadequacy of the outward force generated by the spring devices, in first achieving sealing, and ultimately in maintaining a seal long enough to allow thrombosis to complete the seal. This is true whether the device relies on a coil spring or some other type of spring device for the spring force.

Therefore, it is an object of the present invention to provide a body passageway closure method and apparatus which will provide a large sealing area in a passageway, and which will avoid the rough areas surrounding the ends of the passageway. It is a further object of the present invention to provide a body passageway closure method and apparatus which will seal against the walls of the passageway by means of a sufficiently high force to embed significant portions of the apparatus into the walls of the passageway to retain the apparatus in place. It is a still further object of the present invention to provide a body passageway closure method and apparatus which will permanently deform a portion of the apparatus to create a stable diameter pressed against the walls of the passageway, to result in a secure attachment of the apparatus to the passageway. It is a yet further object of the present invention to provide a body passageway closure method and apparatus which will be easy to implement and relatively economical to manufacture.

SUMMARY OF THE INVENTION

The occluding device of the present invention, as exemplified by a preferred embodiment, includes three basic components. Describing them briefly, first, a substantially cylindrically shaped frame is provided, which can be expanded from a first, relatively small diameter, to a second, relatively large diameter. Second, a sealing membrane or a body made from a blood clot producing substance, such as gel foam, is attached to the frame in an appropriate shape and orientation to occlude the unwanted passageway. Third, a forcible expansion means such as an inflatable balloon is provided inside the frame as a means of expanding the frame with sufficient force to embed portions of the frame in the walls of the passageway. As one basic alternative, the balloon can also function as the sealing membrane.

The expandable frame is constructed of a relatively open structure of elongated elements, which can be achieved in various expandable forms such as a lattice structure, a wire mesh structure, or a coil structure. Such structures are capable of being expanded from a first diameter to a second diameter. The deformation can result in a plastic deformation of the structural elements, so that the frame is converted from a cylinder having a first stable diameter to a cylinder having a second, larger, stable diameter. Alternatively, this permanent expansion of the frame can be achieved by constructing the frame of a substance such as Nitinol, which will undergo a phase change during forcible expansion to stabilize at the larger diameter. As a still further alternative, the frame can be maintained in its expanded state by other means discussed below.

These types of structures, and other similar types, have an added advantage in that they provide numerous elongated structural elements separated by open interstitial spaces, so that when the frame is expanded against the walls of the passageway to be occluded, the elongated elements are at least partially embedded into the walls. This results in secure anchoring of the frame to the passageway walls across a significant area, with each embedded element providing appreciable holding ability. The anchoring function can be promoted by designing portions of the structure to expand outwardly more than surrounding portions. Gaps or weak points can be included in the structure, which will open or break upon expansion, producing exposed edges which result in increased embedment into the passageway walls. The material of the frame can be several types of plastic or metal.

The sealing membrane is preferably very thin, and it can be constructed of several tough but expandable and flexible materials, for example a polyester such as Dacron® by DuPont. The membrane material can be one which will expand by stretching, or it can expand by unfolding. A thrombus promoting substance such as gel foam can also be useful, either as the membrane or as a coating for the membrane, or as a body otherwise attached to the frame or contained by the membrane. An expandable collagen can be used, which will expand upon contact with the blood, and which will subsequently promote blood clotting to block the passageway. The membrane can be provided in several shapes, all of which must be sufficiently thin to offer minimal bulk. It can be an essentially circular shape adhered to the distal end of the frame, or it can be an essentially cylindrical shape covering the sides and ends of the frame.

If the membrane covers the frame, it must be extremely thin in order to avoid impairing the embedment of the frame into the passageway walls. If a circular sealing membrane is attached to the distal end of the frame, it may be necessary to attach a stabilizing membrane to the proximal end of the frame, to ensure that the frame retains its cylindrical shape during expansion.

In some configurations, the sealing membrane will have a very small hole to allow the passage of a guidewire during placement of the occluding device. If the guidewire hole is present, it can be formed through a highly elastic material which will spontaneously seal, or the hole can be sufficiently small that it will seal by spontaneous thrombosis.

The inflatable balloon can be one similar to angioplasty balloons well known in the art for dilatation of blood vessels. Such balloons are commonly deployed on the distal end of a tubular member such as a balloon catheter, or an injectable, hollow guidewire. Such a guidewire has radial and axial strength so as to facilitate movement along the passageway, and it has an inner lumen through which the balloon can be inflated. The balloon is capable of generating sufficiently high force upon expansion to diametrically expand the frame beyond its elastic limit, to achieve an increased, stable, second diameter, and to embed the frame in the passageway walls.

The balloon can be withdrawn from the passageway after expansion of the frame, or it can be left in place to maintain the frame in its expanded state. Maintenance of the expanded diameter by means of the balloon can utilize a check valve on the balloon to capture the fluid pressure, or a hardenable fluid can be injected to achieve and ultimately maintain the expansion. If left in place, the balloon must be delivered in a releasable way, such as on an injectable guidewire, or on a releasable catheter advanced over a removable guidewire.

As mentioned before, the balloon can also act as the sealing membrane. In such a configuration, the balloon must be releasably deployed on a tubular element such as an injectable guidewire. When used as the sealing membrane, the balloon can be adhered to the interior of the frame by use of an adhesive or by heat staking, or the frame can be molded into the wall of the balloon. As other alternatives, the frame ends can be deformed inwardly to capture the balloon, or the frame can be sutured to a portion of the balloon. A retractable sheath can be provided to cover the unexpanded frame during delivery of the frame to the treatment area, to protect the passageway walls by providing a smooth outer surface.

To summarize the use of the apparatus of the present invention, the balloon and the frame, and, where used, the separate sealing membrane, are attached at the distal end of the balloon catheter or the injectable guidewire. The device is advanced, sometimes through a guiding catheter, to the mouth of the passageway to be occluded, and the device is positioned in the passageway, assisted by fluoroscopy. If a protective sheath is used, it is retracted proximally to expose the frame. The appropriate fluid is injected into the balloon, expanding the balloon and the frame until the frame is embedded into the passageway walls.

If the separate sealing membrane is utilized, this expansion step also expands the sealing membrane and the stabilizing membrane. Assuming the frame is designed to be plastically deformed by the expansion step, the balloon is then deflated and withdrawn from the passageway on the end of the catheter, leaving the sealing membrane, the stabilizing membrane, and the frame in place. Alternatively, if the balloon is deployed on an injectable guidewire, the balloon can be released from the injectable guidewire, with the balloon locked at its expanded diameter by means of the check valve, or by means of hardenable fluid.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

Figure 1:
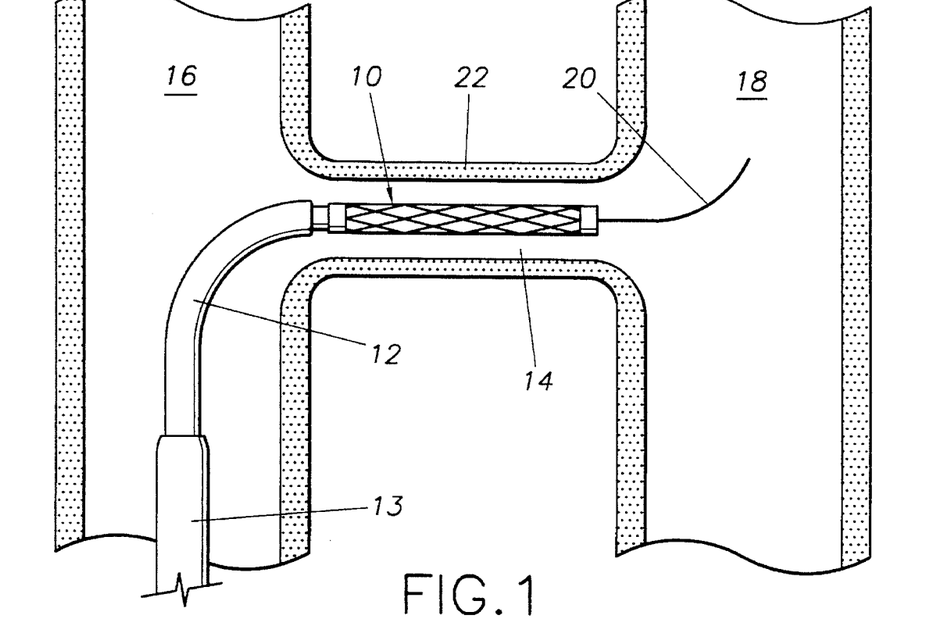
FIG. 1 is a perspective view of the unexpanded body passageway closure of the present invention, with a lattice frame, deployed in a body passageway to be closed.

As seen in FIG. 1, the closure device 10 of the present invention is shown in its intended environment of use, deployed in this instance through a guiding catheter 13 into a patent ductus arteriosus 14. The device 10 is shown in the unexpanded state, as it would be immediately after positioning, and immediately before expansion. For the sake of clarity, a protective sheath 12 is shown here in the retracted position, but if used, the sheath 12 would be disposed to cover the device 10 during delivery into the passageway, while presenting a smooth surface, especially on the distal end. The arterial approach is depicted here, showing the guiding catheter 13 advanced to the area through the aorta 16. Normally, the distal end of the guiding catheter 13 would be advanced all the way to the duct 14, and turned toward the mouth of the duct 14 to guide the device 10 into the duct. For the sake of clarity, in the Figures, the guiding catheter 13 is shown slightly withdrawn from the normal operative position. The passageway or duct 14 to be closed is joined at one end to the aorta 16 and at the other end to the main pulmonary artery 18. The device 10 would typically be advanced over or with a guidewire 20, as is well known in the art of angioplasty. The patent ductus arteriosus environment is shown for illustration purposes only, the present invention also being useful for occluding unwanted passageways of other types.

Figure 2:
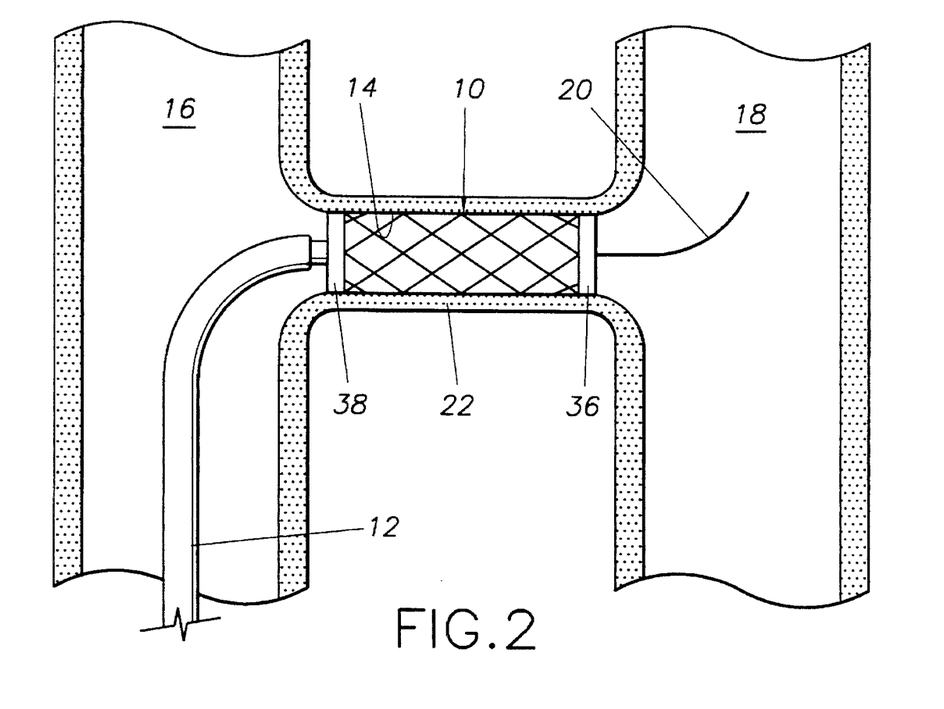
FIG. 2 is a perspective view of the closure device shown in FIG. 1, in the expanded state.

FIG. 2 shows the device 10 in the expanded state, having increased in size diametrically to press firmly against the tubular walls 22 of the passageway 14. The expanded device 10 is shown unchanged in length from the unexpanded state shown in FIG. 1, but it should be understood that some of the types of devices 10 within the scope of the present invention can be designed to decrease or even to increase in length upon expansion. It can be seen from this view that the device 10 has occluded the passageway 14 by contacting the passageway walls 22 over a relatively large area, without contacting the area around the mouth of the passageway at either end, where uneven tissue is likely to be found.

Figure 3:
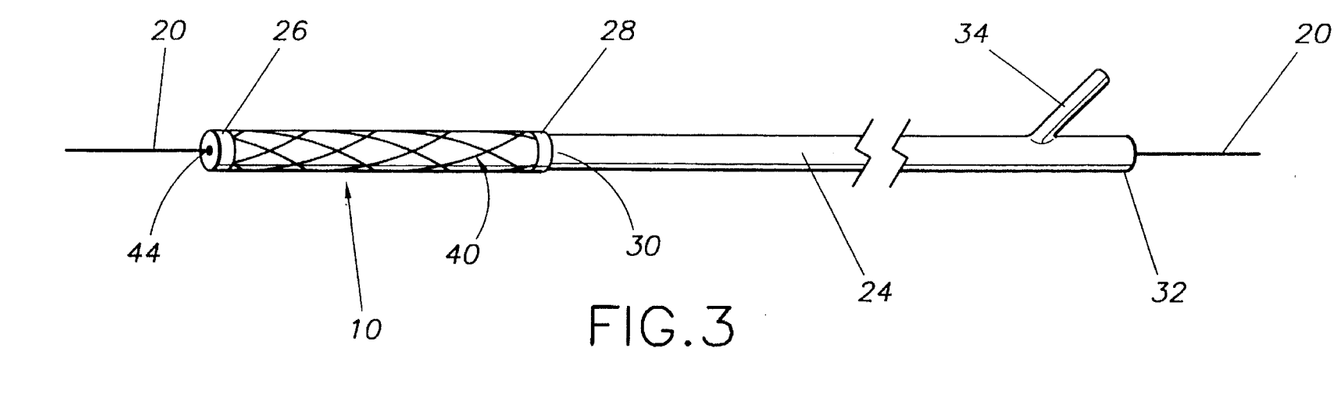
FIG. 3 is a perspective view of the unexpanded closure device shown in FIG. 1, installed on a catheter.

In FIG. 3, it can be seen more clearly that the closure device 10 is attached to a typical balloon catheter tube 24, and that the guidewire 20 runs through the full length of the catheter tube 24 and the device 10. The device 10 could also just as easily be disposed on a rapid exchange catheter, without departing from the present invention. As is well known in the art, this allows the physician to insert the catheter tube 24 and guidewire 20 through the guiding catheter 13, if used, which is inserted into the femoral artery on the leg of the patient, or through the umbilical artery or vein of an infant. The distal end 26 of the closure device 10 becomes essentially the distal end of a balloon catheter, as the proximal end 28 of the closure device 10 is attached to the distal end 30 of the catheter tube 24. This leaves the guidewire 20 extending from the distal end 26 of the closure device 10 and from the proximal end 32 of the catheter tube 24. As can easily be visualized, a rapid exchange catheter could be used, with the guidewire exiting the catheter as is known in the art, proximal to the balloon. A fluid injection port 34 is formed near the proximal end 32 of the catheter tube 24, to provide an access port for injecting fluid at high pressure to expand the closure device 10. As is well known in the angioplasty art, the guidewire 20 typically passes through a different duct within the catheter tube 24 than the duct used to apply the fluid pressure. In some cases, the guidewire will pass alongside a portion of the catheter.

Figure 4:
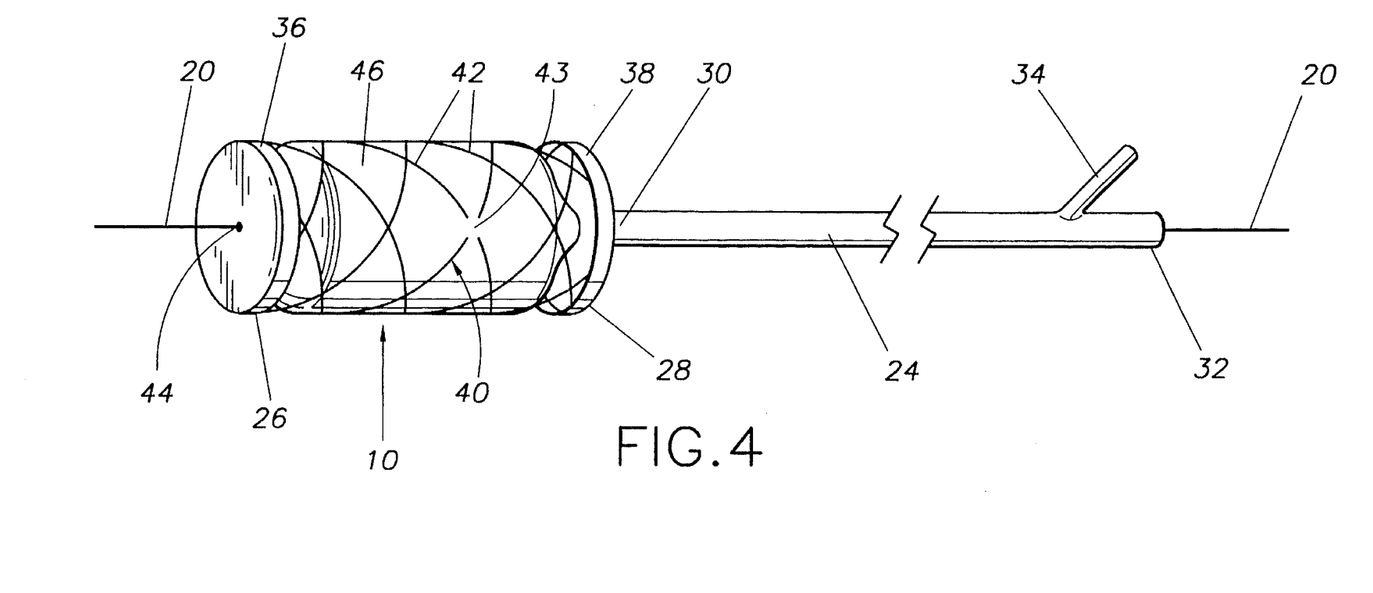
FIG. 4 is a perspective view of the closure device shown in FIG. 3, in the expanded state.

FIG. 4 shows the closure device 10 in the expanded state, with a very thin, expandable sealing membrane 36 attached to the distal end 26 of the device 10, and with a very thin, expandable stabilizing membrane 38 attached to the proximal end 28 of the device 10. Expansion can be by means of stretching of the membrane material or by means of unfolding of the material. The sealing membrane can be formed of a clot promoting material such as gel foam, or it can be coated with such a material. This is also true of the alternative embodiments of the sealing membrane which are to be disclosed hereafter. Also shown more clearly is an expandable frame 40, constructed of a lattice of elongated structural members 42. The lattice structure can be constructed as an expandable network of crossing members, or as an expandable slotted tube, or in other configurations which will result in a lattice type structure upon expansion. As will be mentioned further later, the frame 40 can also be constructed of a mesh structure, or a coil structure, or other similar types of structure. In the preferred embodiment, the frame structure, regardless of the type of construction, can be constructed of plastically deformable elongated elements 42, which will allow the frame 40 to be deformed beyond its elastic limit to achieve a larger, stable diameter. Without departing from the invention, the structure can also be formed of a material which will expand to a second stable diameter without exceeding its elastic limit, such as by undergoing a phase change. In any case, the structure will be capable of changing from one stable diameter to a second, larger, stable diameter. The frame 40 will also be constructed in such a way as to provide numerous structural elements 42 separated by interstitial spaces, to facilitate embedment of the elements 42 into the passageway walls 22 of the passageway 14 to be closed. As an option, the frame 40 can be constructed so as to create a plurality of weak links or gaps 43 which will break or open upon expansion of the frame 40, providing a plurality of sharp points to more deeply embed in the walls 22.

Also shown in FIG. 4 is a very small guidewire port 44 formed in the sealing membrane 36, allowing the guidewire 20 to exit the distal end 26 of the device 10. The guidewire port 44 can be very small to promote sealing upon removal of the guidewire 20, or the port 44 can have a covering to promote sealing.

An inflatable balloon 46 is shown in its expanded state inside the frame 40. The balloon 46 can be formed as a part of a balloon catheter, or if it is desired to leave the balloon 46 in place, it can be releasably attached to an injectable guidewire as will be explained later. Similarly, the balloon 46 can serve as a sealing membrane if desired, as will be shown later. When used as a sealing membrane, the balloon can be formed of, or coated with a clot promoting material. The sealing membrane 36 and the stabilizing membrane 38 are attached to the frame 40, by the use of adhesive, or by other means known in the art, to ensure that the membranes 36, 38 remain in place to perform their respective sealing and stabilizing functions. The stabilizing membrane 38 holds the frame 40 in the cylindrical configuration during expansion by restricting the proximal end 28, counterbalancing the restrictive effect of the sealing membrane 36 at the distal end 26. This stabilization ensures that the frame 40 is not forced off of the distal end of the balloon 46 during expansion. When in the unexpanded state shown in FIG. 3, the balloon 46, the frame 40, and the membranes 36, 38 can be compacted to a small, stable diameter which will pass to the body passageway to be closed, with ease.

Figure 5:
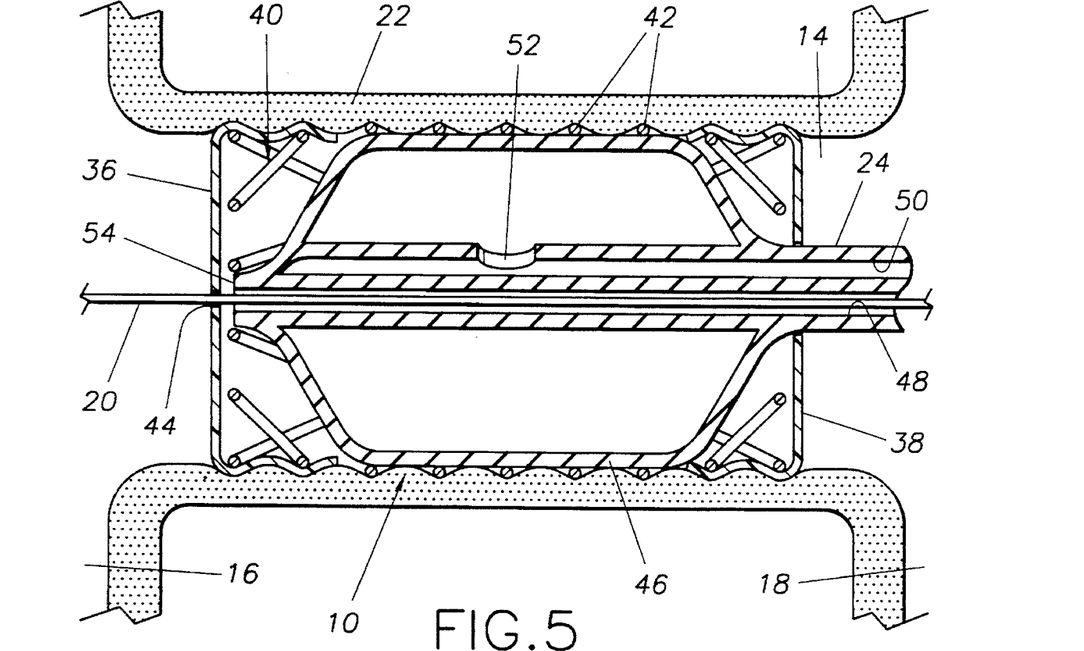
FIG. 5 is a section view of the closure device of the present invention, as expanded in a passageway.

FIG. 5 shows a section view of the closure device 10 as installed and expanded in the passageway 14. The internals of a typical balloon 46 are shown, with the guidewire 20 passing through the guidewire duct 48 and out the distal end 54 of the balloon 46. The fluid injection port 34 leads to an injection fluid duct 50 which leads ultimately to a balloon port 52 inside the balloon 46. The balloon 46 is shown expanded; therefore, at this point, the frame 40 is expanded to the second stable dimension attainable by the elongated lattice elements 42. This causes the frame 40 to assume a second, larger, stable diameter as shown. This expanded diameter is sufficiently large to embed portions of the elongated lattice elements 42 in the walls 22 of the passageway 14. It can be seen that, where the membranes 36, 38 overlap the frame 40, the membranes 36, 38 are sufficiently thin to allow the lattice elements 42 to embed in the passageway walls 22. This embedment of the lattice elements 42 in the passageway walls 22 causes the closure device 10 to be firmly retained in the passageway 14. The breaks or gaps 43 expose edges which will more securely embed in the passageway walls 22. Since the sealing membrane 36 is firmly adhered to the frame 40, the passageway 14 will be effectively occluded.

Figure 6:
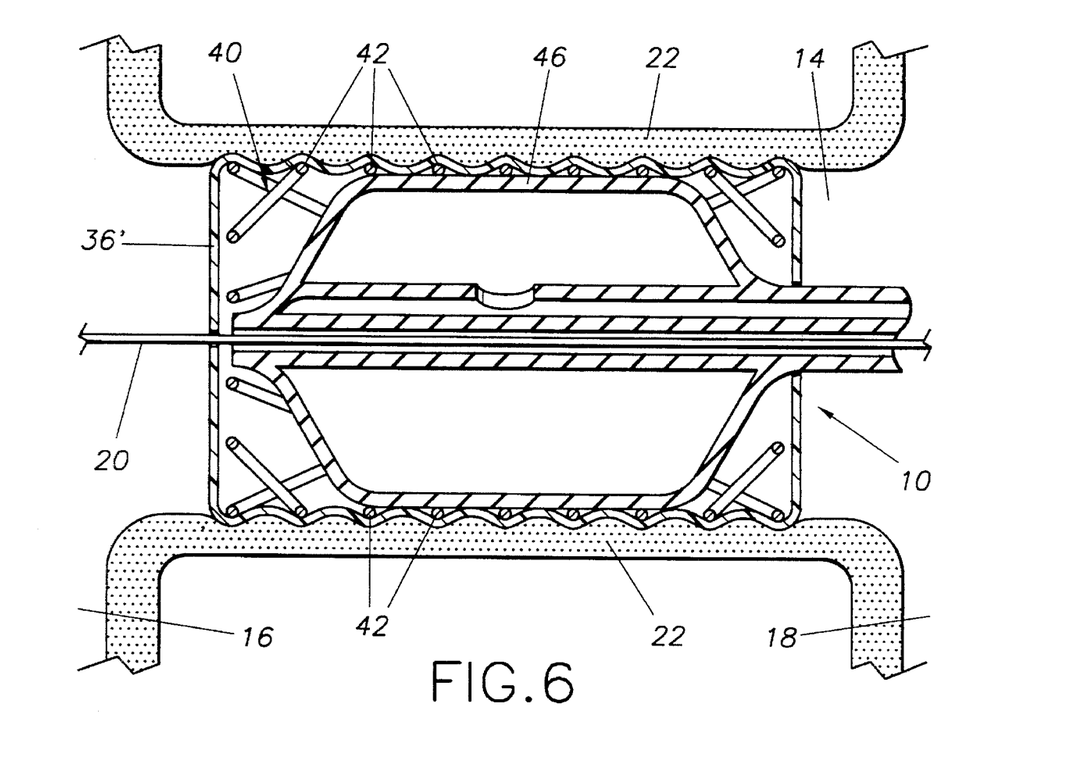
FIG. 6 is a section view of an alternate embodiment of the present invention.

FIG. 6 shows an alternative embodiment of the present invention, where the sealing membrane 36' takes the shape of an expandable sealing cylinder formed on the outside of the frame 40. In the version shown here, the inflatable balloon 46 is still used to expand the frame 40 as discussed before. The sealing membrane 36' is retained on the frame 40 by being formed around the outside of the frame 40, and the sealing membrane 36' is sufficiently thin to allow the lattice elements 42 to embed in the passageway walls 22. When the frame 40 has been expanded, the inflatable balloon 46 is deflated and removed. Alternatively, as mentioned before, the balloon 46 can be introduced on the distal end of an injectable guidewire; in that case, the balloon 46 can be released from the guidewire and left in place.

Figure 7:
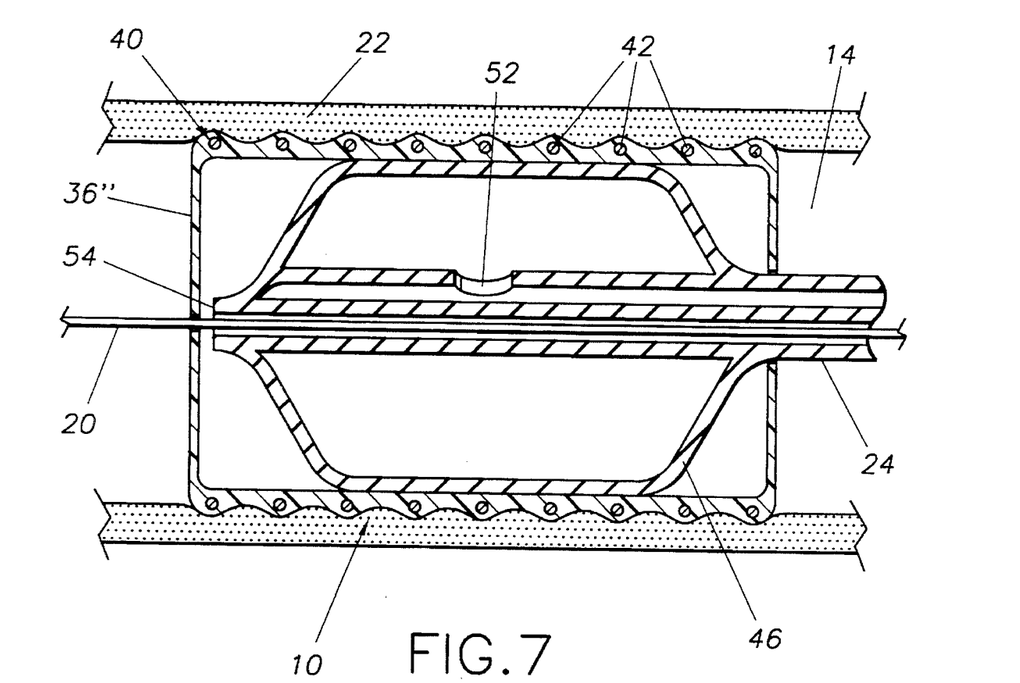
FIG. 7 is a section view of a second alternate embodiment of the present invention.

FIG. 7 shows another alternative embodiment of the closure device 10 wherein the expandable sealing membrane 36" is again formed as a sealing cylinder. This version effects the retention of the sealing membrane 36" on the frame 40 by having the lattice elements 42 molded within the wall of the membrane 36". As can be seen, the membrane material covering the lattice elements 42 is sufficiently thin to allow embedment of the lattice elements 42 in the passageway walls 22. Here again, the inflatable balloon 46 can be removed or left in place as required.

Figure 8:
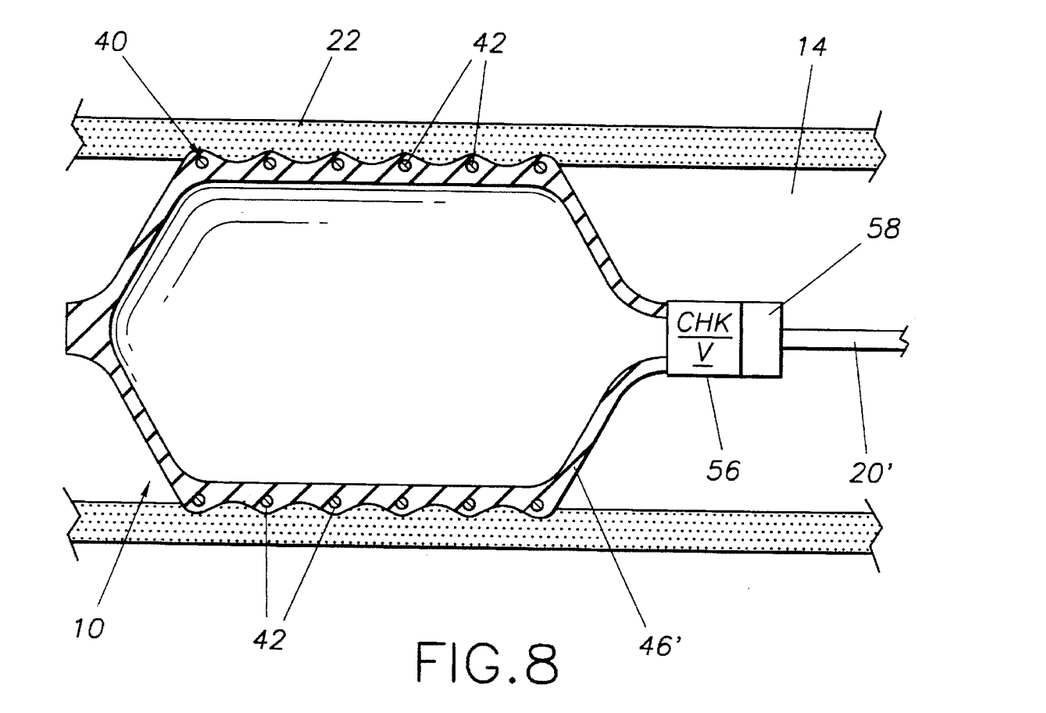
FIG. 8 is a section view of a third alternate embodiment of the present invention.

FIG. 8 shows yet another alternative embodiment, in which the inflatable balloon 46' also serves as the sealing membrane. In this version, the lattice elements 42 are molded into the walls of the inflatable balloon 46', with the balloon material overlying the lattice elements 42 being sufficiently thin to allow embedment of the lattice elements 42 in the passageway walls 22. In this version, of course, the inflatable balloon 46' must be left in place after the expansion of the frame 40. Therefore, the pressurized fluid is introduced into the balloon 46' through a hollow injectable guidewire 20', as is known in the art. The frame 40 can be maintained in its expanded state by being stretched beyond its elastic limit, or the expanded diameter can be maintained by keeping the balloon 46' at its expanded diameter. The balloon 46' can be locked in the expanded state by having a check valve 56 to capture the fluid pressure inside the balloon 46'. Alternatively, the balloon 46' can be filled and expanded with a hardenable fluid. After expansion, the balloon 46' is released by means of a balloon release 58, such as a screw release mechanism, or other mechanisms known in the art. This permits the withdrawal of the injectable guidewire 20'.

Figure 9:
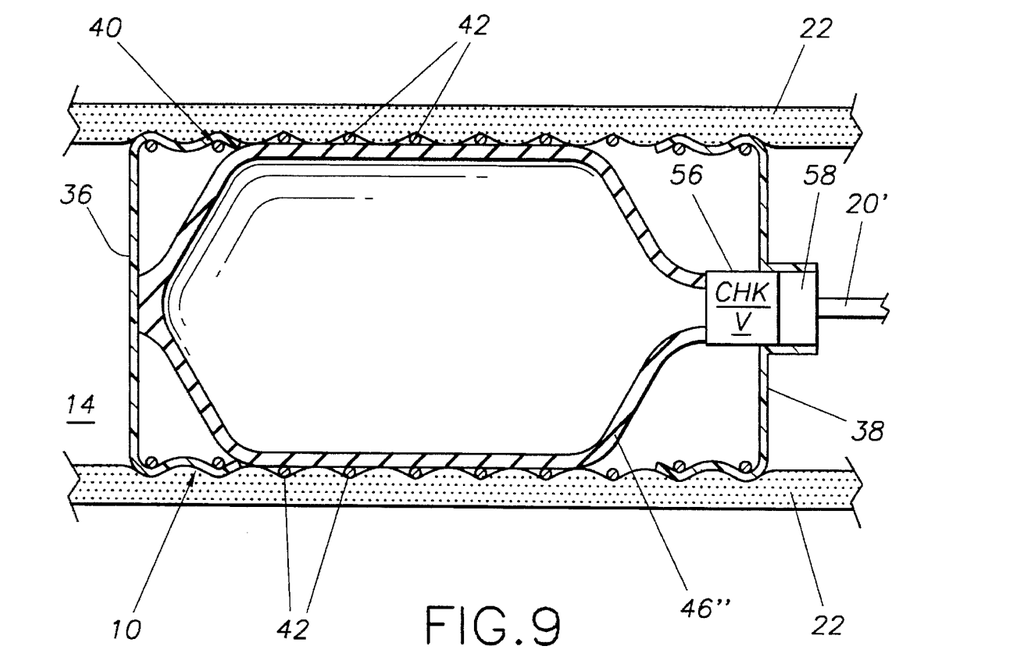
FIG. 9 is a section view of a fourth alternate embodiment of the present invention.

Still further, FIG. 9 shows another alternative embodiment of the closure device 10, in which a sealing membrane 36 and a stabilizing membrane 38 are used as before. In this version, the expansion of the frame 40 is to be maintained by leaving the inflatable balloon 46" in place, so the inflatable balloon 46" is fitted with a check valve 56 and a balloon release 58. This allows the device 10 to be advanced into the body passageway and inflated on the injectable guidewire 20', followed by withdrawal of the guidewire 20'.

Figure 10:
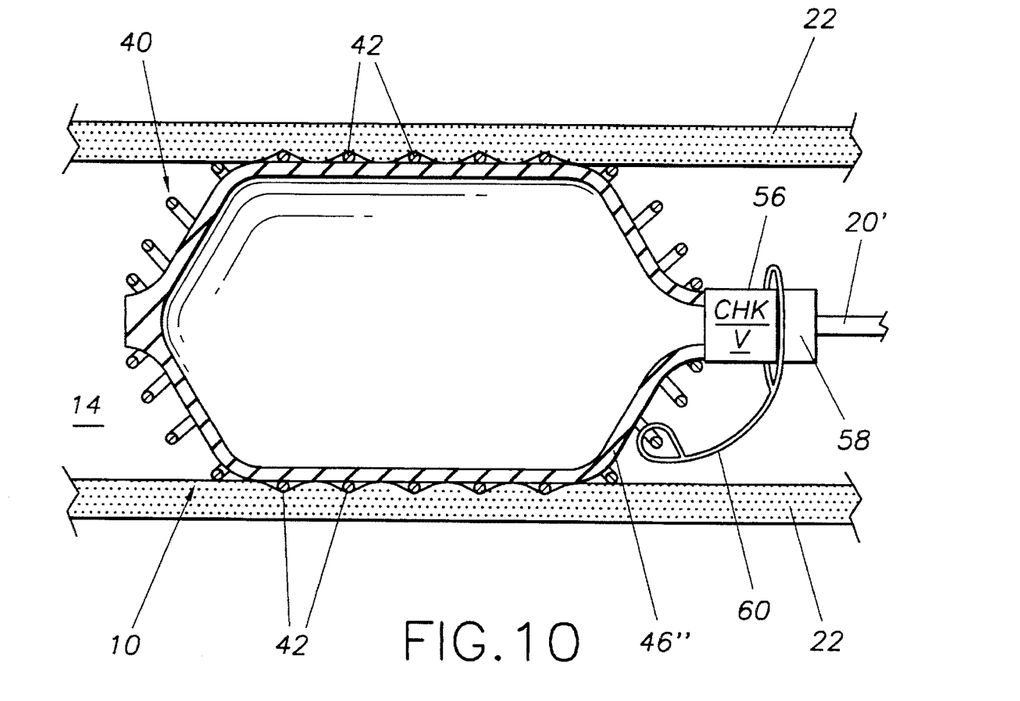
FIG. 10 is a section view of a fifth alternate embodiment of the present invention.

FIG. 10 shows another embodiment in which the inflatable balloon 46" is delivered and inflated on an injectable guidewire 20', which can then be released and withdrawn, leaving the balloon 46" inflated and serving as a sealing membrane. The frame 40 is formed inwardly at the ends to enclose and capture the balloon 46", to retain the balloon 46" to the frame 40, thereby retaining the balloon 46" in the passageway 14. The balloon 46" can also optionally be adhered to the frame 40, or the balloon 46" can be tethered to the frame 40 with a suture 60, or both.

Figures 11, 12:
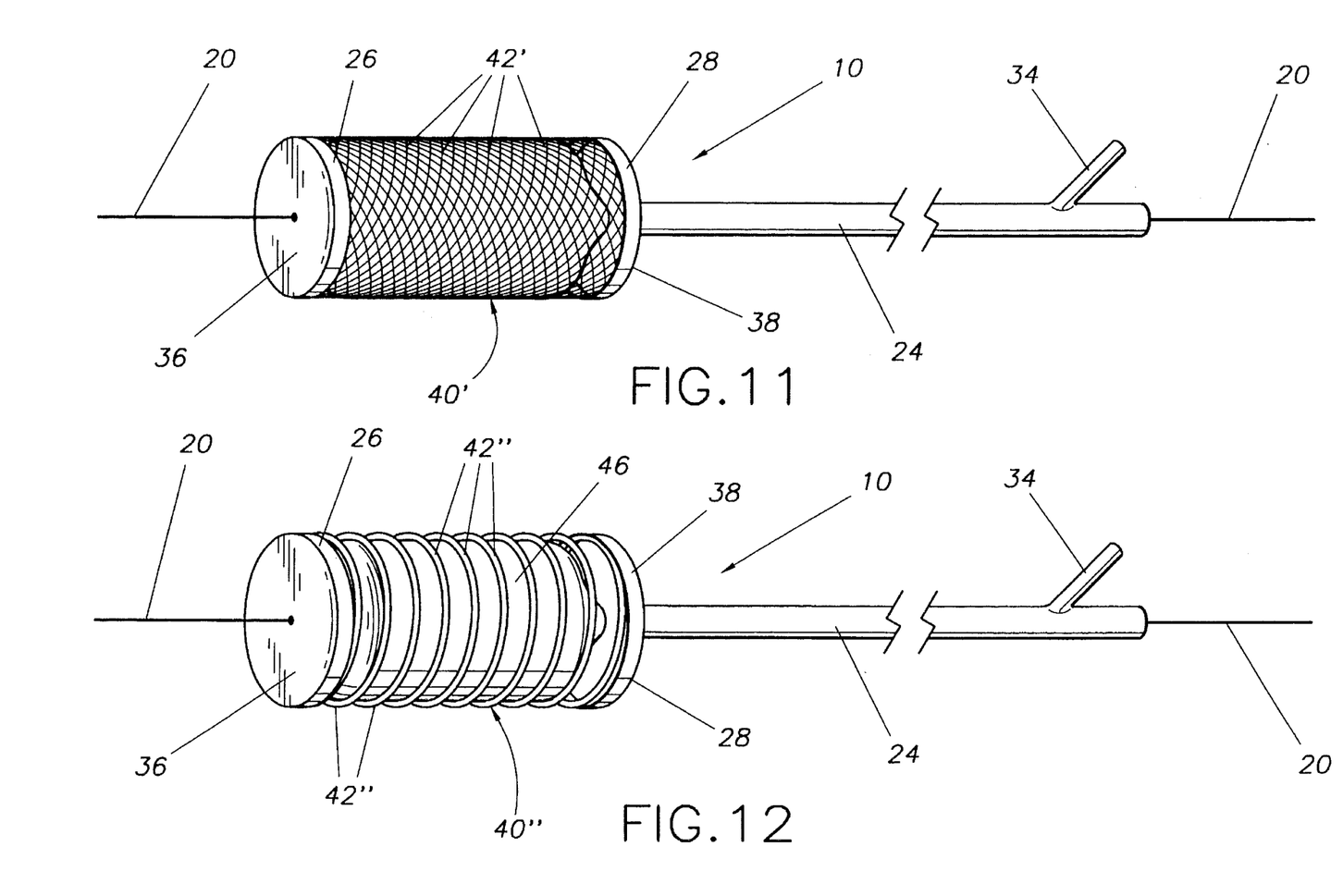
FIG. 11 is a perspective view of the closure device shown in FIG. 3, with a mesh frame, in the expanded state.
FIG. 12 is a perspective view of the closure device shown in FIG. 3, with a coil frame, in the expanded state.

FIG. 11 shows an alternative version of the closure device 10 in which the device 10 is mounted on a catheter 24, and in which a sealing membrane 36 and a stabilizing membrane 38 are used. In this version, the frame 40' is formed of a mesh fabric which performs in all pertinent respects the same as the aforementioned lattice structure. The mesh fabric is constructed of elongated mesh elements 42' with numerous interstitial spaces, allowing the elongated elements 42' of the fabric to be embedded in the passageway walls 22 for anchoring purposes. The mesh fabric can be constructed to be plastically deformable, or the frame 40' can be maintained in the expanded state by the inflatable balloon 46. As with the lattice frame 40, the mesh frame 40' can be used with a releasable balloon 46", or with a catheter balloon 46. Also, the mesh frame 40' can be positioned on the inside of a cylindrical sealing membrane 36', formed into a cylindrical sealing membrane 36", or formed into an inflatable balloon 46'.

Another embodiment of the closure device 10 with a coil frame 40" is shown in FIG. 12. The coil frame 40" is capable of all the different applications described for the lattice frame 40 and the mesh frame 40'. The coil frame 40" can be formed with a multiple stranded coil made of multiple elongated coil elements 42" which can embed in the passageway walls 22.

Figure 13:
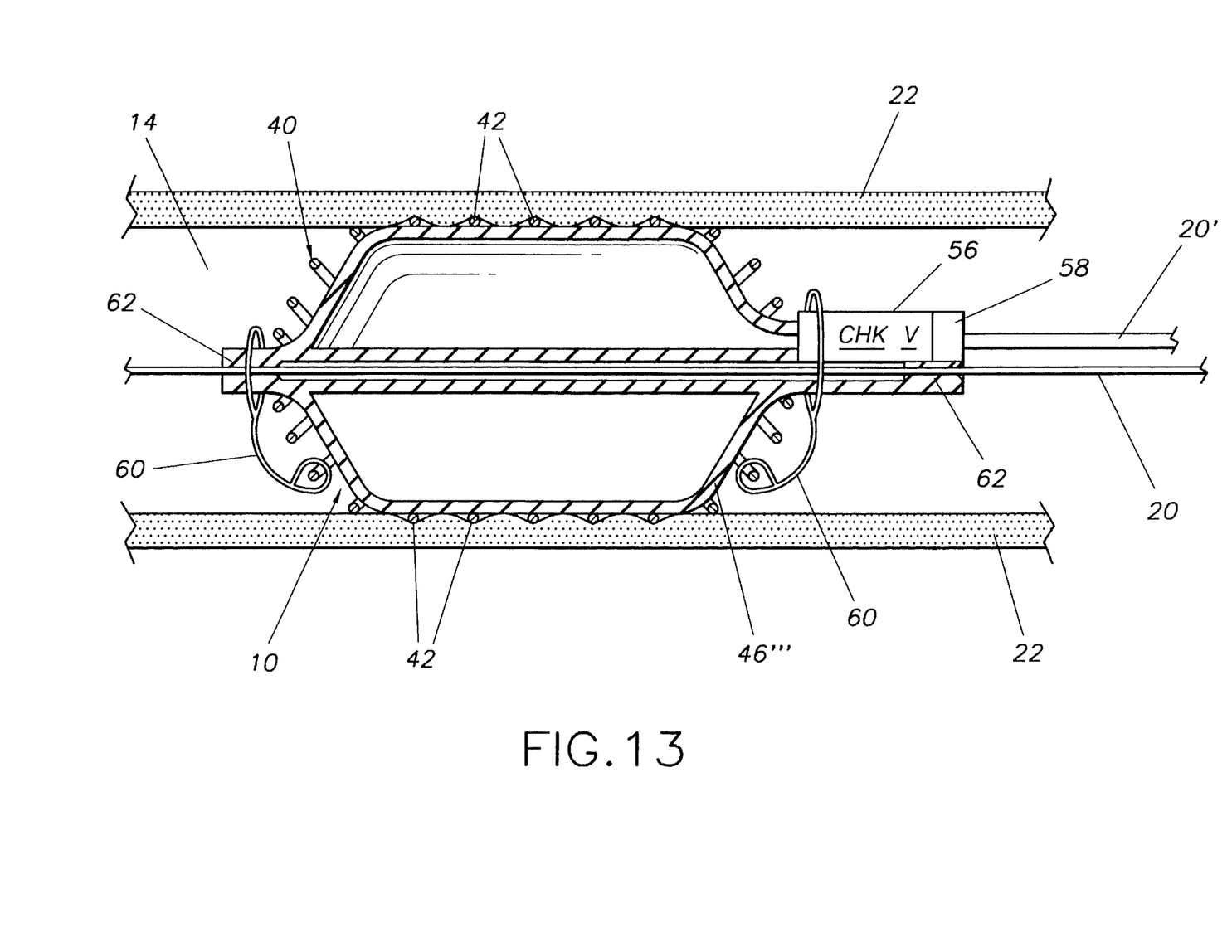
FIG. 13 is a section view of a sixth alternate embodiment of the present invention.

FIG. 13 shows yet another embodiment in which the inflatable balloon 46''' is delivered over a conventional guidewire 20. The guidewire 20 penetrates a pair of self sealing membranes 62 at the distal and proximal ends of the balloon 46'''. The balloon 46''' is advanced and inflated by an injectable guidewire 20' or other tubular member, which can then be released and withdrawn, along with the conventional guidewire 20, leaving the balloon 46''' inflated and serving as a sealing membrane. The frame 40 is formed inwardly at the ends to enclose and capture the balloon 46''', to retain the balloon 46''' to the frame 40, thereby retaining the balloon 46''' in the passageway 14. The balloon 46''' can also optionally be adhered to the frame 40, or the balloon 46''' can be tethered to the frame 40 with sutures 60, or both.

OPERATION

The closure device 10 of the present invention is affixed to either a balloon catheter 24 or an injectable guidewire 20', depending upon whether the balloon is to be left in place or retrieved. The device 10 is then advanced into the body passageway 14, as is well known in the art of angioplasty, aided by fluoroscopy. Once positioned in the passageway 14, the protective sheath 12 is retracted, and the balloon 46, 46', 46" is inflated to expand the frame 40, 40', 40" and embed the frame in the walls 22 of the passageway 14. This expansion can plastically deform the frame 40, 40', 40" so that it will maintain its expanded diameter, and the balloon 46 can be withdrawn with the catheter 24. Alternatively, the balloon 46', 46" can be left in place to maintain the expanded frame diameter and seal the passageway 14, and the injectable guidewire 20' can be withdrawn.

While the particular Body Passageway Closure as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A device for closure of a body passageway of a patient, comprising:

an expandable, substantially cylindrical frame;

expansion means for selectively applying force to diametrically expand said frame to embed portions of said frame into a wall of the passageway, for retention of said frame in the passageway;

a flexible sealing membrane permanently retained on said frame to occlude the passageway upon said expansion of said frame; and delivery means for delivering said frame and said sealing membrane to a selected site in the passageway to be occluded, said delivery means being removable from the passageway after said delivery, leaving said frame and said sealing membrane in place.

2. A device for closure of a body passageway, as claimed in claim 1, wherein said cylindrical frame is plastically deformable from a first stable diameter to a second stable diameter.

3. A device for closure of a body passageway, as claimed in claim 1, wherein said expansion means comprises:

an expandable balloon;

a tubular means incorporated in said delivery means, said tubular means being detachably connectable to said balloon for selective application of fluid pressure to expand said balloon, said tubular means being removable from the passageway along with said delivery means after detachment from said balloon; and means for maintaining said expansion of said balloon upon detachment of said tubular means from said balloon.

4. A device for closure of a body passageway, as claimed in claim 3, wherein said means for maintaining said expansion comprises a nonreturn valve mounted on said balloon for connection of said tubular means.

5. A device for closure of a body passageway, as claimed in claim 3, wherein said means for maintaining said expansion comprises a fluid injectable through said tubular means, said fluid being capable of transforming to a solid within the patient's body passageway.

6. A device for closure of a body passageway, as claimed in claim 1, wherein said frame comprises a cylindrical lattice structure.

7. A device for closure of a body passageway, as claimed in claim 1, wherein said frame comprises a cylindrical mesh structure.

8. A device for closure of a body passageway, as claimed in claim 1, wherein said frame comprises a cylindrical coil structure.

9. A device for closure of a body passageway, as claimed in claim 1, wherein said expansion means comprises:

an inflatable balloon insertable within said frame; and a catheter attached to said balloon for selective application of fluid pressure to expand said balloon.

10. A device for closure of a body passageway, as claimed in claim 1, wherein said embedded portions of said frame comprise at least one structural element sufficiently separated from surrounding elements of said frame to partially extend into the wall of the passageway.

11. A device for closure of a body passageway, as claimed in claim 10, wherein said structural element comprises an elongated lattice element.

12. A device for closure of a body passageway, as claimed in claim 10, wherein said structural element comprises an elongated mesh element.

13. A device for closure of a body passageway, as claimed in claim 10, wherein said structural element comprises an elongated coil element.

14. A device for closure of a body passageway, as claimed in claim 1, wherein:

said sealing membrane occludes the passageway at a first end of said frame; and said sealing membrane is retained on said frame by being fastened to said frame at said first end of said frame.

15. A device for closure of a body passageway, as claimed in claim 14, further comprising a flexible stabilizing membrane, said stabilizing membrane being retained on said frame by being fastened to said frame at a second end of said frame.

16. A device for closure of a body passageway, as claimed in claim 1, wherein said flexible sealing membrane comprises an expandable balloon.

17. A device for closure of a body passageway, as claimed in claim 16, wherein said expansion means comprises a tubular means detachably connected to said balloon for selective application of fluid pressure to expand said balloon.

18. A device for closure of a body passageway, as claimed in claim 16, wherein said balloon is retained within said frame by being fastened to said frame.

19. A device for closure of a body passageway, as claimed in claim 16, wherein a first end and a second end of said frame are formed around said balloon to retain said balloon within said frame.

20. A device for closure of a body passageway, as claimed in claim 16, wherein said frame is molded within the wall of said balloon.

21. A device for closure of a body passageway, as claimed in claim 1, wherein said flexible sealing membrane comprises a blood clot promoting substance.

22. An apparatus for closure of a body passageway, comprising:
   a source of fluid pressure;
   a flexible catheter connectable to said fluid pressure source, said catheter having a distal end insertable into the passageway to be closed;
   an inflatable balloon connected in fluid communication with said distal end of said catheter for the selective application of said fluid pressure to expand said balloon;
   an expandable, substantially cylindrical frame mountable on said balloon for diametrical expansion by said balloon to partially embed said frame into a wall of the passageway, for retention of said frame in the passageway, said frame being plastically deformable from a first stable diameter to a second stable diameter, said balloon being removable from said frame upon deflation of said balloon;
   a flexible sealing membrane permanently retained on a distal end of said frame to occlude the passageway upon said expansion of said frame;
   a flexible stabilizing membrane permanently retained on a proximal end of said frame to maintain said frame in a substantially cylindrical configuration during said expansion; and
   a passageway through said stabilizing membrane for said catheter.

23. A device for closure of a body passageway, as claimed in claim 22, wherein said flexible sealing membrane comprises a blood clot promoting substance.

24. An apparatus for closure of a body passageway, comprising:
   a source of fluid pressure;
   a flexible tubular member connectable to said fluid pressure source, said tubular member having a distal end insertable into the passageway to be closed;
   an inflatable balloon connected in fluid communication with said distal end of said tubular member for the selective application of said fluid pressure to expand said balloon to occlude the passageway;
   an expandable, substantially cylindrical frame mounted on said balloon for diametrical expansion by said balloon to partially embed said frame into a wall of the passageway, for retention of said frame in the passageway;
   means for selectively releasing said balloon from said tubular member;
   means for maintaining said frame in said expanded state; and
   means for retaining said balloon to said frame in the passageway.

25. A device for closure of a body passageway, as claimed in claim 24, wherein said balloon comprises a blood clot promoting substance.

26. A method for closing a body passageway, comprising the steps of:
   providing an expansion means;
   mounting an expandable, substantially cylindrical frame to said expansion means;
   permanently attaching a flexible sealing membrane to said frame, to occlude said passageway upon expansion of said frame;
   inserting said expansion means, said frame, and said sealing membrane into the body passageway until said sealing membrane and said frame are positioned at the point where the passageway is to be closed;
   expanding said frame to partially embed said frame in the walls of the passageway to retain said frame and said sealing membrane in the passageway; and
   removing said expansion means from the passageway.

27. A device for closure of a body passageway, as claimed in claim 26, wherein said sealing membrane comprises a blood clot promoting substance.

28. A method for closing a body passageway, as claimed in claim 26, further comprising the step of locking said frame in said expanded state prior to removing said expansion means from the passageway.

29. A method for closing a body passageway, as claimed in claim 28, wherein the step of locking said frame in said expanded state comprises the step of plastically deforming said frame during said expansion of said frame.

30. A method for closing a body passageway, as claimed in claim 28, wherein:
   the step of expanding said frame comprises the step of applying fluid pressure to expand a balloon within said frame; and
   the step of locking said frame in said expanded state comprises the step of capturing said fluid pressure in said balloon.

31. A method for closing a body passageway, as claimed in claim 28, wherein:
   the step of expanding said frame comprises the step of applying fluid pressure to expand a balloon within said frame; and
   the step of locking said frame in said expanded state comprises the step of hardening said fluid in said balloon.

32. A method for closing a body passageway, as claimed in claim 26, wherein said expansion means comprises a tubular member, the method further comprising the step of mounting an expandable balloon at a distal end of said tubular member for expansion by fluid pressure.

33. A method for closing a body passageway, as claimed in claim 32, further comprising the step of removing said balloon from the passageway along with said tubular member.

34. A method for closing a body passageway, as claimed in claim 32, further comprising the step of detaching said balloon from said tubular member prior to removing said tubular member from the passageway.

35. A method for closing a body passageway, as claimed in claim 26, wherein said sealing membrane comprises a balloon expandable by fluid pressure and detachable from said expansion means.

36. A device for closure of a body passageway, comprising:

an expandable, substantially cylindrical frame;

expansion means for selectively applying force to diametrically expand said frame to embed portions of said frame into a wall of the passageway, for retention of said frame in the passageway; and a flexible sealing membrane retained on said frame to occlude the passageway upon said expansion of said frame;

wherein said flexible sealing membrane comprises a blood clot promoting substance.

37. An apparatus for closure of a body passageway, comprising:

a source of fluid pressure;

a flexible catheter connectable to said fluid pressure source, said catheter having a distal end insertable into the passageway to be closed;

an inflatable balloon connected in fluid communication with said distal end of said catheter for the selective application of said fluid pressure to expand said balloon;

an expandable, substantially cylindrical frame mountable on said balloon for diametrical expansion by said balloon to partially embed said frame into a wall of the passageway, for retention of said frame in the passageway, said frame being plastically deformable from a first stable diameter to a second stable diameter;

a flexible sealing membrane retained on a distal end of said frame to occlude the passageway upon said expansion of said frame;

a flexible stabilizing membrane retained on a proximal end of said frame to maintain said frame in a substantially cylindrical configuration during said expansion; and a passageway through said stabilizing membrane for said catheter;

wherein said flexible sealing membrane comprises a blood clot promoting substance.

38. An apparatus for closure of a body passageway, comprising:

a source of fluid pressure;

a flexible tubular member connectable to said fluid pressure source, said tubular member having a distal end insertable into the passageway to be closed;

an inflatable balloon connected in fluid communication with said distal end of said tubular member for the selective application of said fluid pressure to expand said balloon to occlude the passageway;

an expandable, substantially cylindrical frame mounted on said balloon for diametrical expansion by said balloon to partially embed said frame into a wall of the passageway, for retention of said frame in the passageway;

means for selectively releasing said balloon from said tubular member;

means for maintaining said frame in said expanded state; and means for retaining said balloon to said frame in the passageway;

wherein said balloon comprises a blood clot promoting substance.

39. A method for closing a body passageway, comprising the steps of:

providing a tubular member;

mounting a balloon on a distal end of said tubular member;

mounting an expandable, substantially cylindrical frame to said balloon;

inserting said distal end of said tubular member into the body passageway until said balloon and said frame are positioned at the point where the passageway is to be closed;

applying fluid pressure through said tubular member to expand said balloon, thereby expanding said frame to partially embed said frame in the walls of the passageway to retain said frame in the passageway; and removing said tubular member from the passageway;

wherein said balloon comprises a blood clot promoting substance.

40. A method for closing a body passageway, comprising the steps of:

providing a tubular member;

mounting a balloon on a distal end of said tubular member;

mounting an expandable, substantially cylindrical frame to said balloon;

inserting said distal end of said tubular member into the body passageway until said balloon and said frame are positioned at the point where the passageway is to be closed;

applying fluid pressure through said tubular member to expand said balloon, thereby expanding said frame to partially embed said frame in the walls of the passageway to retain said frame in the passageway;

hardening said fluid in said balloon to lock said frame in said expanded state;

removing said tubular member from the passage way.

* * * * *

(12) REEXAMINATION CERTIFICATE (4542nd)
United States Patent
Teirstein (10) Number: US 5,499,995 C1
(45) Certificate Issued: Mar. 12, 2002

(54) BODY PASSAGEWAY CLOSURE APPARATUS AND METHOD OF USE

(75) Inventor: Paul S. Teirstein, 402 Coast Blvd., South, La Jolla, CA (US) 92037

(73) Assignee: Paul S. Teirstein, La Jolla, CA (US)

Reexamination Request:
No. 90/005,210, Jan. 6, 1999

Reexamination Certificate for:
Patent No.: 5,499,995
Issued: Mar. 19, 1996
Appl. No.: 08/249,521
Filed: May 25, 1994

(51) Int. Cl.[7] ............................................. A61M 29/00
(52) U.S. Cl. ...................................... 606/192; 606/194

(56) References Cited

U.S. PATENT DOCUMENTS

| | | | | |
|---|---|---|---|---|
| 4,619,261 A | | 10/1986 | Guerriero | 128/325 |
| 4,686,985 A | * | 8/1987 | Lottick | 128/344 |
| 4,733,665 A | * | 3/1988 | Palmaz | 604/104 |
| 4,739,762 A | * | 4/1988 | Palmaz | 604/104 |
| 5,102,417 A | * | 4/1992 | Palmaz | 604/8 |
| 5,116,318 A | * | 5/1992 | Hillstead | 604/96 |
| 5,382,261 A | | 1/1995 | Palmaz | 606/158 |

FOREIGN PATENT DOCUMENTS

| | | |
|---|---|---|
| DE | 40 28 466 A1 | 3/1992 |
| DE | 92 05 797.7 | 7/1992 |
| EP | 0 375 775 | 7/1990 |
| WO | WO 93/13712 | 7/1993 |

\* cited by examiner

Primary Examiner—Michael Anthony Brown (57) ABSTRACT

A method and apparatus for blocking a body passageway by inserting an expandable frame into the passageway and expanding the frame with an expandable balloon to partially embed the frame in the walls of the passageway. The frame can carry a separate sealing membrane, or the balloon can function as the sealing membrane. The sealing membrane, the frame or the balloon can also carry a clot promoting substance. The balloon can be removed along with the inflation tube after the expansion procedure, if it is not serving as the sealing membrane, or the balloon can be detached from the inflation tube and left in place, either as a sealing membrane or simply to lock the frame in place. The frame can be maintained in its expanded state by being plastically deformed during the expansion step, or the frame can be maintained in its expanded state by having the balloon locked in the expanded state and left in place.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3–5, 7–8, 12–13, 15–25, 27, 30–31 and 34–40 is confirmed.

Claims 1–2, 6, 9–11, 14, 26, 28–29 and 32–33 are cancelled.

* * * * *